United States Patent [19]

Ojima et al.

[11] Patent Number: 5,569,246
[45] Date of Patent: Oct. 29, 1996

[54] FIXING INSTRUMENT FOR SPINAL FUSION MEMBERS

[75] Inventors: Satoshi Ojima, Tokyo; Shoji Uchida, Hyogo-ken, both of Japan

[73] Assignee: Asahi Kogaku Kogyo Kabushiki Kaisha, Tokyo, Japan

[21] Appl. No.: 364,464

[22] Filed: Dec. 27, 1994

[30] Foreign Application Priority Data

Dec. 28, 1993 [JP] Japan ................. 5-074709 U

[51] Int. Cl.⁶ ..................... A61B 17/70; A61B 17/80
[52] U.S. Cl. ............................. 606/61; 606/69
[58] Field of Search ................. 606/72, 73, 69, 606/70, 71, 61, 60

[56] References Cited

U.S. PATENT DOCUMENTS

| | | | |
|---|---|---|---|
| 5,084,049 | 1/1992 | Asher et al. | 606/61 |
| 5,147,361 | 9/1992 | Ojima et al. | |
| 5,176,680 | 1/1993 | Vignaud et al. | 606/61 |
| 5,334,203 | 8/1994 | Wagner | 606/61 |
| 5,391,168 | 2/1995 | Sanders et al. | 606/61 |

OTHER PUBLICATIONS

Stuart Spine Division Product Brochure entitled "Instruments for Proper Implantation," dated Nov. 1992.
Dir Co. Ltd. Product Brochure entitled "Spinal Fixation Diapason," published by Dismo Innovation Research in English and Japanese.

*Primary Examiner*—Michael Powell Buiz
*Assistant Examiner*—Scott B. Markow
*Attorney, Agent, or Firm*—Greenblum & Bernstein P.L.C.

[57] ABSTRACT

Two posterior spinal fusion members are secured to a plurality of vertebrae which constitute a spine. The posterior spinal fusion members are fixed to both sides of the spinous processes of the vertebrae. A fixing instrument is attached to each posterior spinal fusion member. The fixing instrument includes a rod-shaped connecting member and two hooks slidably attached to both ends of the connecting member. Elongated holes are formed in the portions of the connecting member where the hooks are attached. Male screws are driven through the elongated holes. The surface around the opening of each elongated hole where the head of the associated male screw slides is formed as the bottom of a recess which is shallow on the associated end side of the fixing instrument and is deep on the connecting member side. When a hexagonal wrench is inserted in a hexagonal hole formed in the end face of the head of this male screw and is manipulated to drive the male screw into the associated hook, the head of the male screw slides on the bottom of this recess, causing the hook to move toward the connecting member. Therefore, force is applied to the two posterior spinal fusion members to shift the posterior spinal fusion members toward each other.

15 Claims, 6 Drawing Sheets

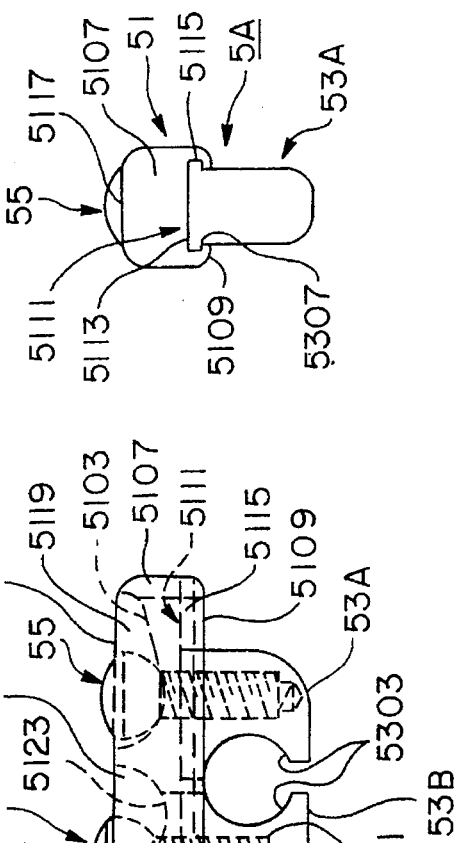
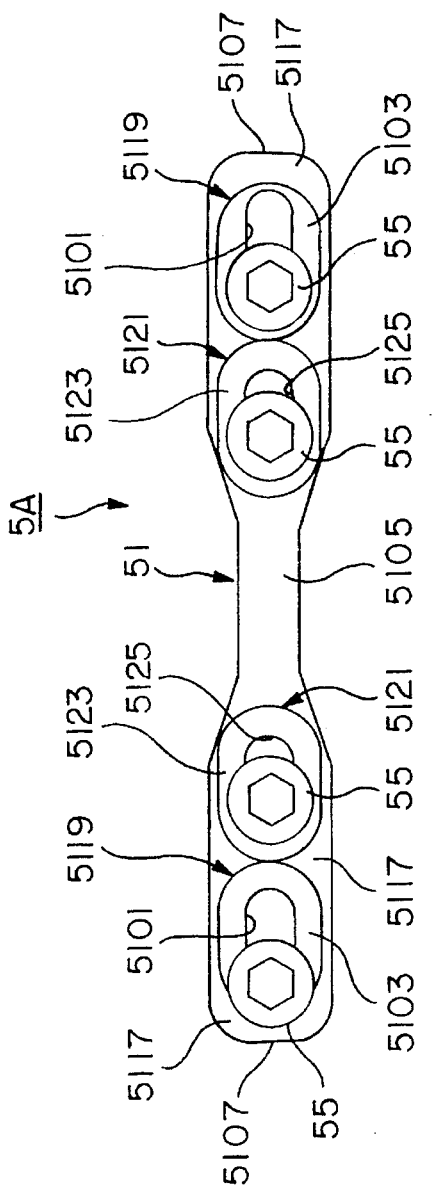
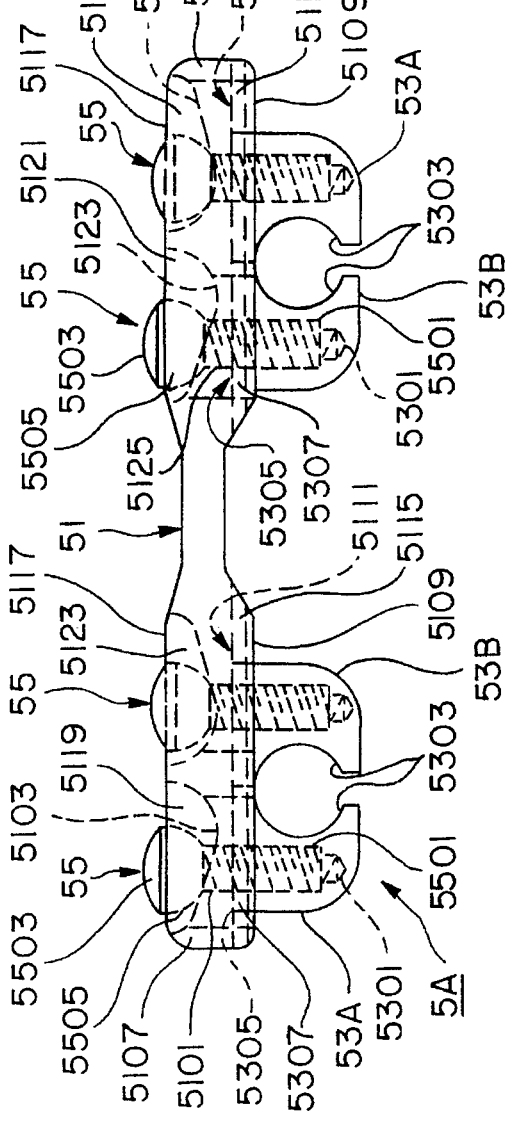

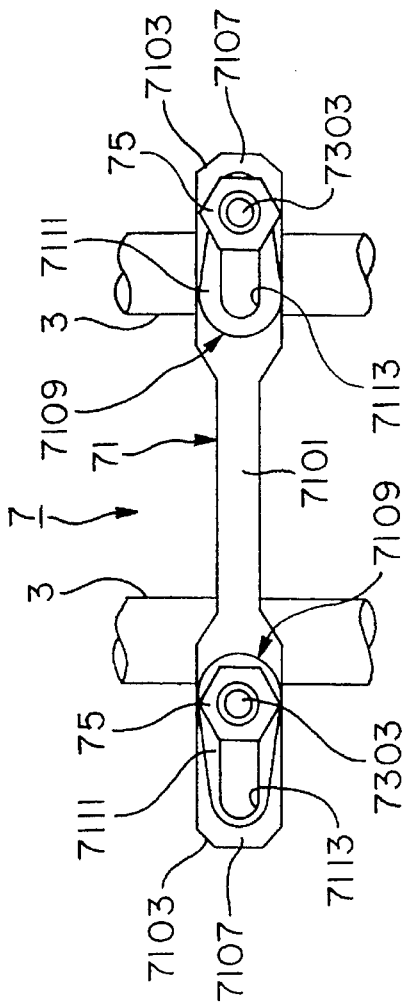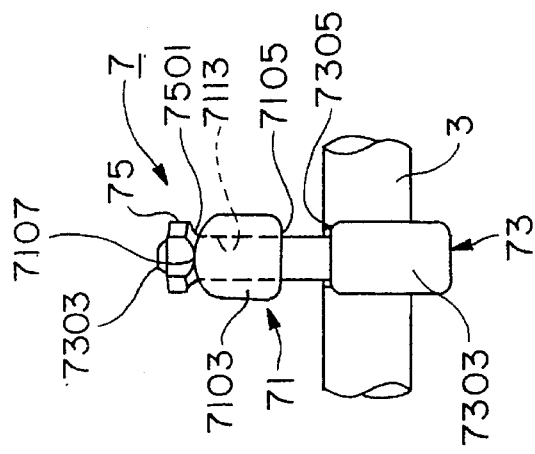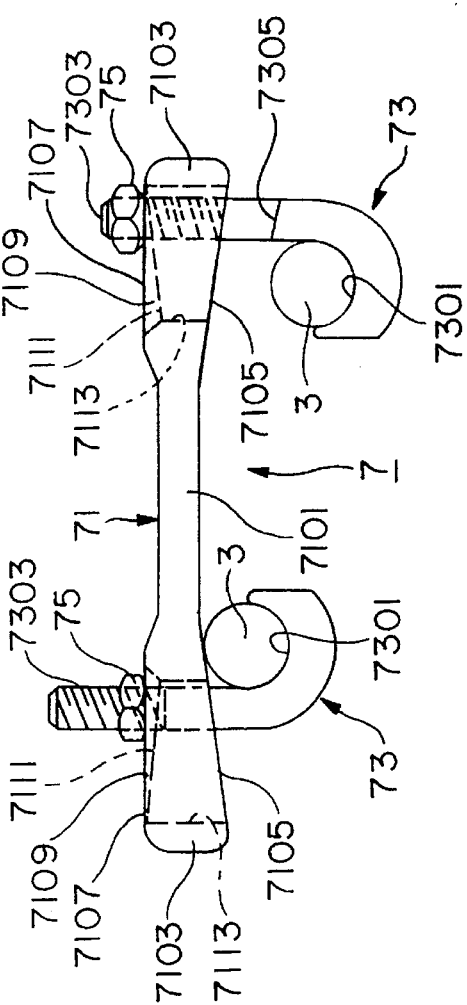

FIXING INSTRUMENT FOR SPINAL FUSION MEMBERS

BACKGROUND OF THE INVENTION

1. Field of the Invention

The present invention relates to a fixing instrument for a spinal fusion member that is used to secure spinal fusion members together, which are attached to both sides of a spine to correct a distortion of the spine.

2. Description of the Related Art

As one treatment for patients who suffer from spondylolisthesis, abnormal curvature of the spine and the like, corpus vertebrae which constitute a distorted spine are coupled together vertically by an elongated spinal fusion member and the distortion is corrected by the rigidity of the spinal fusion member.

In this case, a surgeon dissects the back of a patient to expose the vertebrae. Then, the spinal fusion members are fixed on the both sides of each of the vertebrae with screws secured to lengthwisely apart portions of the spinal fusion members.

Further, to correct the distortion of the spine in the twisting direction, a screw structure is laid out with the axis of the screw perpendicular to both spinal fusion members to apply them force in the direction approaching each other.

According to this method, however, only the peripheral surface of the screw Structure faces the dissected portion of a patient. Fastening the screw therefore requires gradual turning of a wrench in a narrow space formed in the patient's body by dissection, thus making the surgical operation troublesome.

SUMMARY OF THE INVENTION

A primary object of the present invention is to provide a fixing instrument for spinal fusion members, which is easily manipulatable, even if provided in a narrow space formed in a patient's body by dissection, from outside the body to apply force to both spinal fusion members to cause them to approach each other, thus contributing to simplification of a surgical operation.

To achieve the above object, according to this invention, there is provided a fixing instrument for mutually fixing a plurality of spinal fusion members to be secured over a plurality of vertebrae constituting a spine. The fixing instrument includes a connecting member to be laid across the plurality of spinal fusion members, a plurality of engagement members having engaging portions to engage with the spinal fusion members and provided on the connecting member slidably along the lengthwise direction thereof, moving members movable in a direction toward the corresponding engagement member, one end of each of the moving members positioned at the opposite side of the connecting member to the side where the engagement members are provided, and a conversion mechanism for converting the movement of the moving members to a one-way sliding movement of the engagement members in a direction approaching the corresponding spinal fusion member.

BRIEF DESCRIPTION OF THE DRAWINGS

The invention will be described below in detail with reference to the accompanying drawings in which:

FIG. 4 is a cross-sectional view along the line IV—IV in. FIG. 1;

FIGS. 6a, 6b and 6c are, respectively, a plan view, a front view and a side view showing the structure of a fixing instrument according to a second embodiment of the invention shown in FIG. 1; and FIGS. 7a, 7b and 7c are, respectively, a plan view, a front view and a side view showing the structure of a fixing instrument according to a third embodiment of the invention shown in FIG. 1.

DETAILED DESCRIPTION OF THE PREFERRED EMBODIMENTS

The present disclosure relates to subject matter contained in Japanese utility model Application No. 5-74709 (filed on Dec. 28, 1993), which is expressly incorporated herein by reference in its entirety.

Preferred embodiments of the present invention will now be described referring to the accompanying drawings.

FIRST EMBODIMENT

Figure 4:
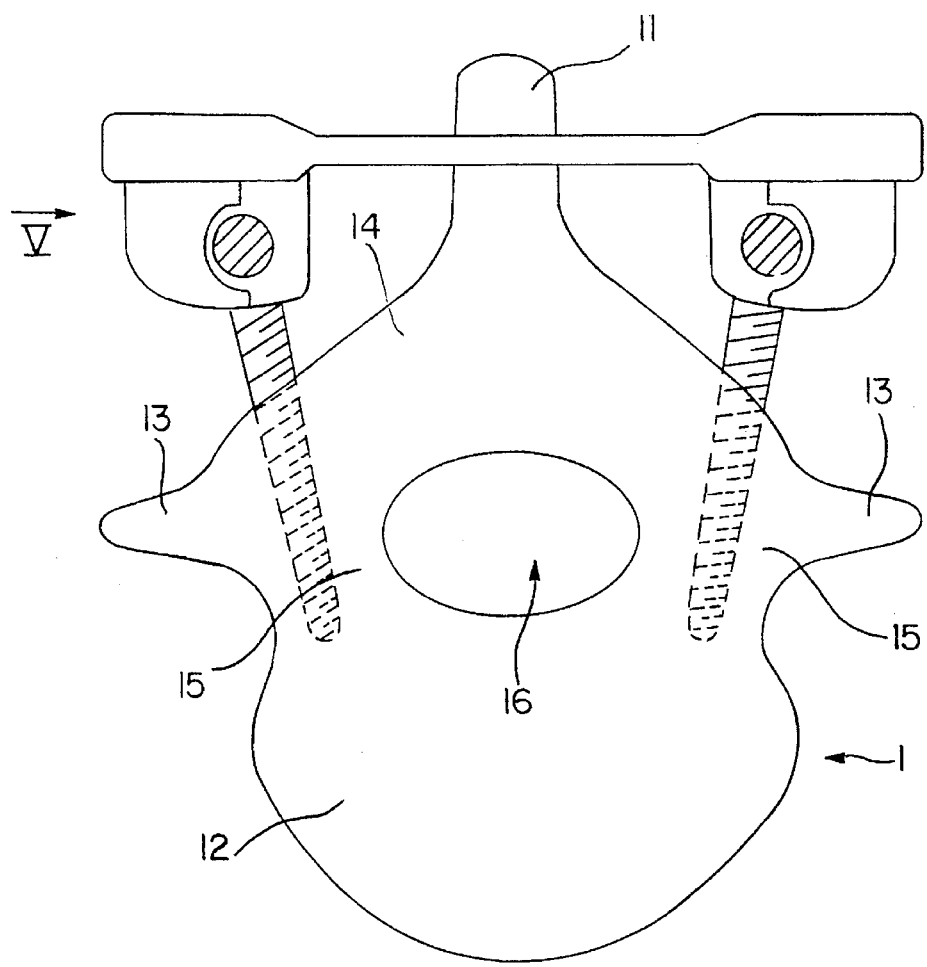

Before describing posterior spinal fusion members according to this embodiment, names of each parts of individual vertebra 1 constituting a spine will be explained with reference to FIG. 4. FIG. 4 shows a single vertebra 1 viewed from above (from the head side). A columnar corpus vertebra 12 is formed on front side (abdominal side) of the vertebra 1. The corpus vertebra 12 is connected to the corpus vertebrae 12 of upper and lower adjoining vertebrae 1 via intervertebral disks. Formed at the rear side (dorsal side) of the corpus vertebra 12 is an arcus vertebra 14 which has an arcuate shape. The space defined between the arcus vertebra 14 and the Corpus vertebra 12 is a vertebral canal 16 in which a spinal cord runs. The portion where the arcus vertebra 14 is joined to the corpus vertebra 12 is called a pediculus arcus vertebra 15. A spinous process 11, protrudes rearward from the center portion of the arcus vertebra 14. The pot%ions which project substantially sideward from right and left sides of the arcus vertebra 14 are called transverse process 13.

Figure 1:
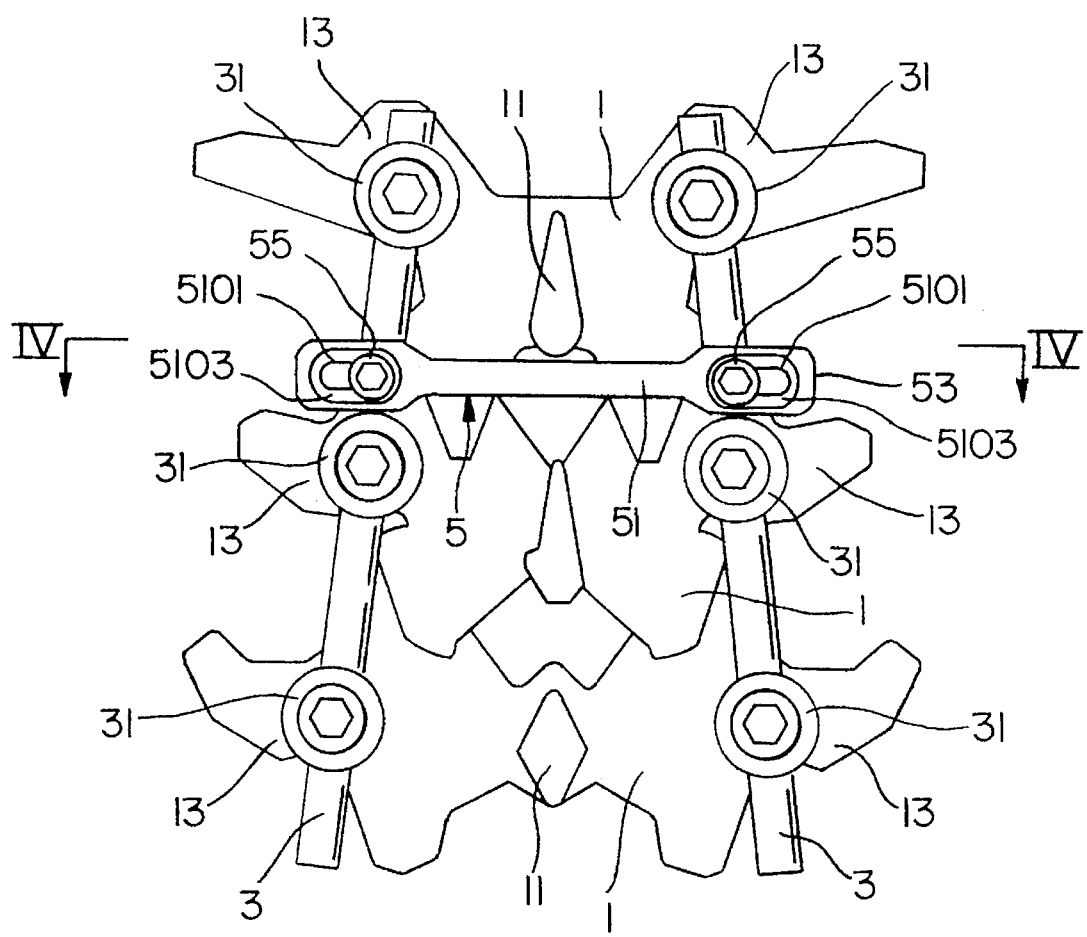
FIG. 1 is an explanatory diagram showing a fixing instrument for posterior spinal fusion members according to a first embodiment of the invention in use.

FIG. 1 shows the spine constituted of the above-described vertebrae 1 from the dorsal side. FIG. 1 also shows two posterior spinal fusion members 3 and fixing instrument 5 according to this embodiment which are attached to the spinal column. The posterior spinal fusion members 3 ere secured by screws on the surfaces of the individual arcus vertebrae 14 which are both sides of the spinous processes 1 over a plurality of vertically arranged vertebrae 1. More specifically, the posterior spinal fusion members 3 are fixed by screws at the positions of caps 31 shown in FIG 1. The fixing instrument 5 having hooks (see FIG. 2) is anchored to both posterior spinal fusion members 3 with the hooks. 53 hooked on the associated posterior spinal fusion members 3. Each hook 53 is hooked on the associated posterior signal fusion member 3.

A description will now be given of the structure of each posterior spinal fusion member 3 and the structure for securing the posterior spinal fusion member S with reference to FIG. 3.

Figure 3:
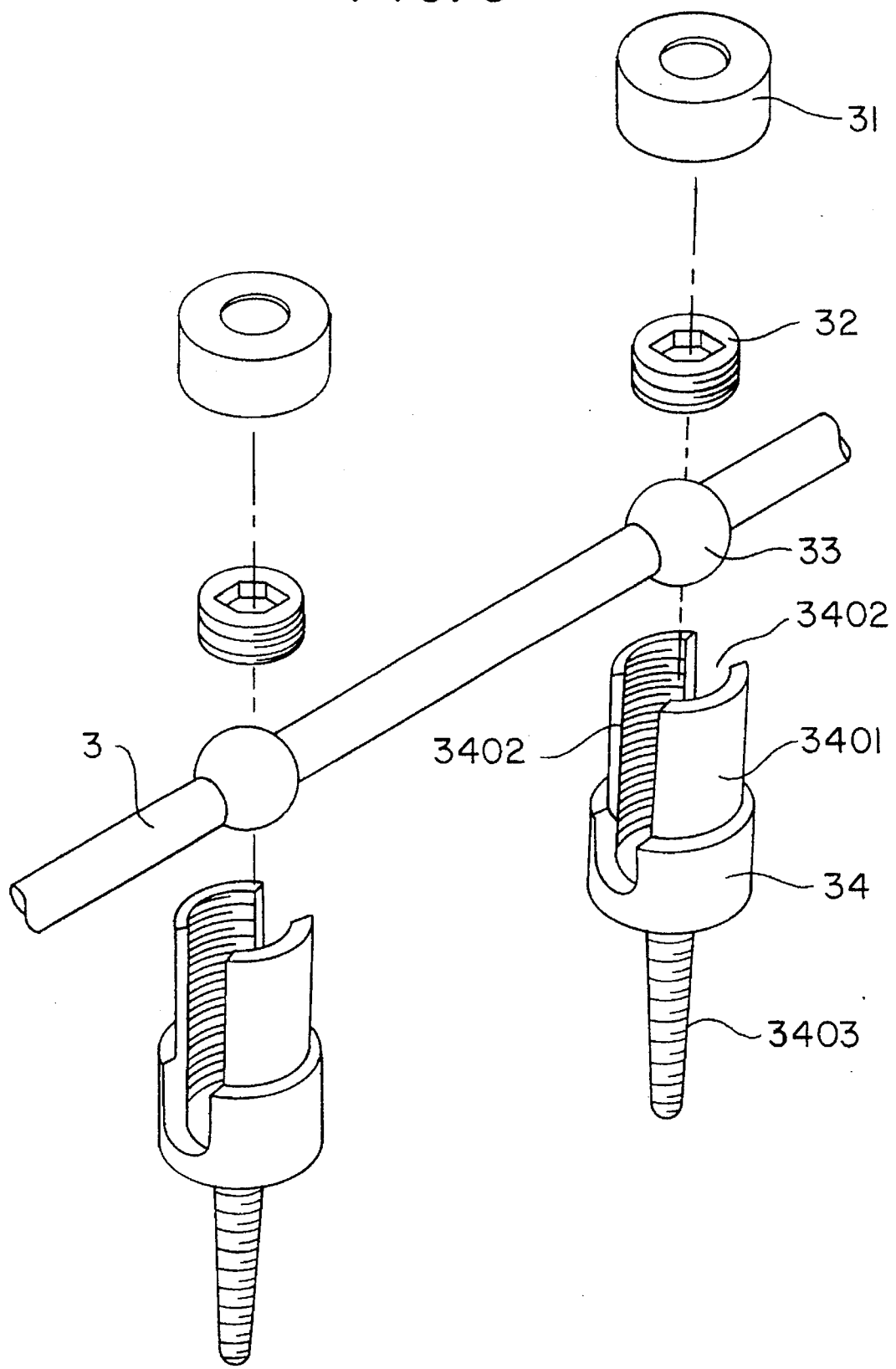
FIG. 3 is an exploded perspective view of a posterior spinal fusion member according to the first embodiment of the invention.

As shown in FIG. 3, the posterior spinal fusion member 3 has a rod shape and has a plurality of washers 33 fixed at equal intervals along the axis thereof. Each washer 33 has a spherical surface. A pedicular screw 34 secures the posterior spinal fusion member 3 to the vertebra 1.

The pedicular screw 34 has a cylinder portion 3401 at the top thereof. The inner diameter of the cylinder portion 3401 is larger than the outer diameter of the washer 33. The washers 33 are therefore positioned in the associated cylinder portions 3401. Formed in the cylinder portion 3401 of the pedicular screw 34 is a slit 3402 whose width is wide enough to pass the posterior spinal fusion member 3, but not the washer 33. That is, the cylinder portion 3401 has a forked shape. Female threads are formed in the inner wall of the cylinder portion 3401. Male threads 3403 formed at the distal end of the pedicular screw 34 form a tapered screw.

A disk shaped setscrew 32 has male threads formed on the outer surface, which engage the female threads on the inner wall of the associated cylinder portion 3401. Formed in the center of the upper end of each setscrew 32 is a hexagonal hole where a hexagonal wrench is insertable. Accordingly, with the posterior spinal fusion member 3 and the washers 33 fitted in the cylinder portions 3401, as the setscrews 32 are engaged with the associated cylinder portions 3401, the movement of the posterior spinal fusion member 3 is checked.

The caps 31 are put over the distal ends of the associated cylinder portions 3401 to protect the internal organs from the edges of the distal ends of the cylinder portions 3401. Each cap 31 has a hole at the center thereof, through which the hexagonal wrench passes to drive the setscrew.

Figure 2A:
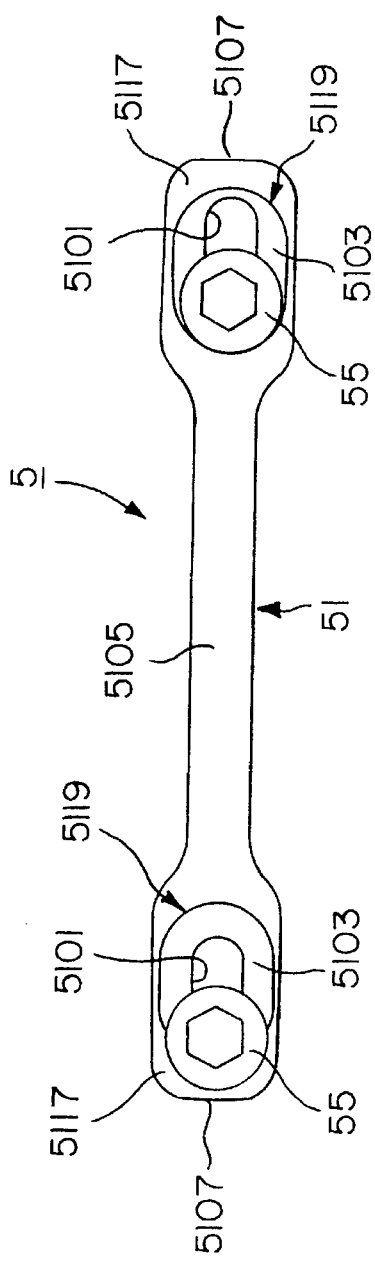
FIGS. 2a, 2b and 2c are, respectively, a plan view, a front view and a side view showing the structure of the fixing instrument according to the first embodiment of the invention shown in FIG. 1.
Figure 2C:
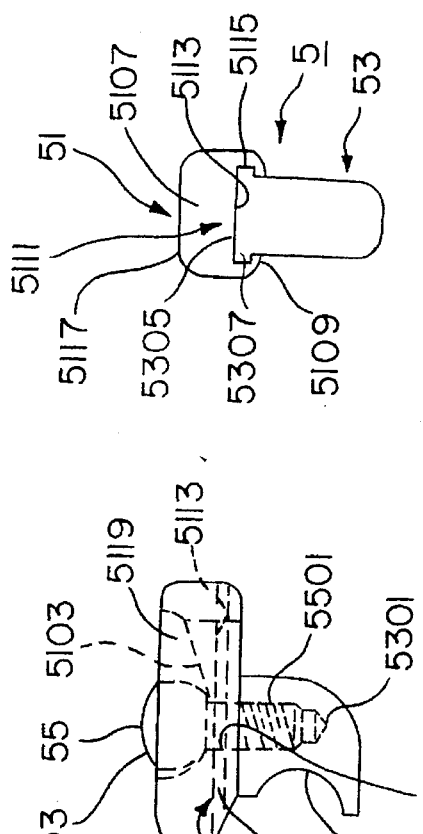
Figure 2B:
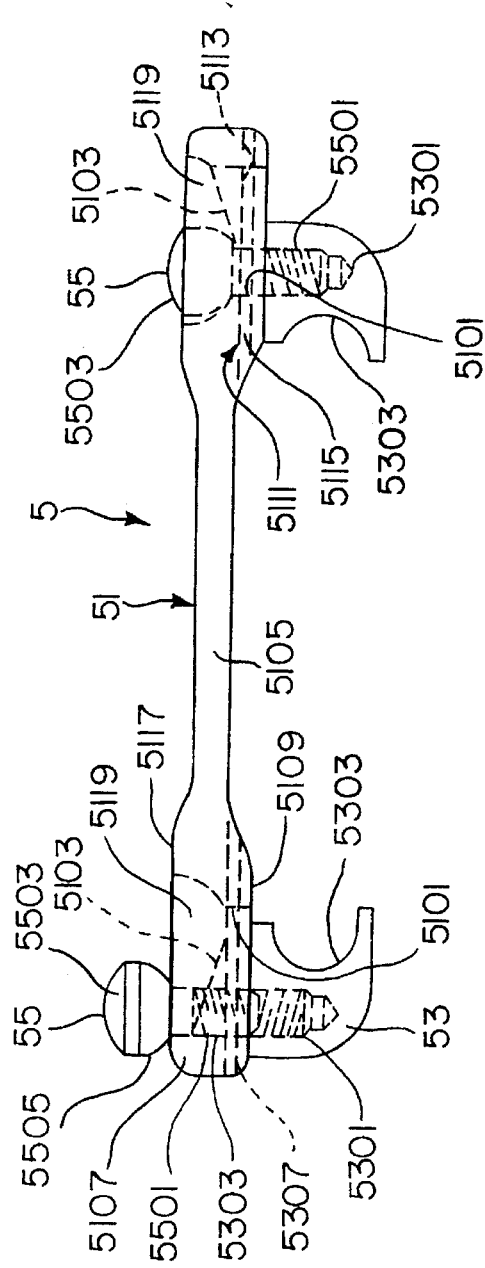

The fixing instrument 5 includes a connecting member 51 having a length corresponding to the distance between the pair of posterior spinal fusion members 3, and a pair of hooks (corresponding to engagement members) coupled to both ends of the connecting member 51, as shown in FIGS. 2a, 2b and 2c. A coupling mechanism for coupling the hook 53 to the connecting member 51 includes an elongated hole 5101 formed in either end of the connecting member 51, a screw hole 5301 formed in the hook 53, a screw or mounting member 55, slide grooves 5115, slide projections 5307 and an inclined surface 5103. The individual parts of the securing instrument 5 will be described below.

The connecting member 51 has a rod-like shaft portion 5105 and hook support portions 5107 formed as flat square rods at both ends of the shaft portion 5105. An engagement recess 5111 is formed in a bottom surface 5109 of each hook support portion 5107 as a straight groove elongated along the lengthwise direction of the shaft portion 5105. The engagement recess 5111 has a flat bottom surface 5113 on both sides of which a pair of parallel elide grooves 5115 are formed facing each other. A recess 5119 is formed in a top surface 5117 of each hook support portion 5107 in an oval shape of which major axis is laid along the lengthwise direction of the shaft portion 5105. The aforementioned inclined surface 5103 is formed as the bottom surface of the recess 5119. The inclined surface 5103 is shallower on the side which is closer to the end of the securing instrument 51, and is deeper on the side which is closer to the shaft portion 5105. Further, the elongated hole 5101 is formed in the widthwise center of the inclined surface 5103 elongated along the lengthwise direction of the shaft portion 5105. The elongated hole 5101 reaches the engagement recess 5111 through the hook support portion 5107.

Each hook 53 has an arched engagement surface 5303 engageable with the associated posterior spinal fusion member 3. The straight slide projections 5307, which engage with the slide grooves 5115 of the engagement recess 5111, are formed on both sides of the proximal end of each hook 53. The screw hole 5301 is formed in substantially center of a flat surface 5305 at the proximal end of each hook 53.

The screw 55 has a male thread portion 5501, which engages with the screw hole 5301 of the hook 53, and a head 5503. The outside diameter of the head 5503 is slightly smaller than the width of the engagement surface 5103 of the recess 5119 and is larger than the width of the elongated hole 5101. The head 5503 has a hemispherical bottom surface 5505. When the head 5503 is located closer to the shaft portion 5105 in the recess 5119, most of the head 5503 is retained in the recess 5119. Formed in the end face of the head 5503 is a hexagonal hole where a hexagonal wrench is insertable.

To attach the hook 53 to the hook support portion 5107, the slide projections 5307 and flat surface 5305 at the problem end of the hook 53 are respectively engaged with the slide grooves 5115 and flat surface 5113 of the hook support portion 5107. At this time, the directions of both hooks 53 are adjusted in such a way that the engagement surfaces 5303 of the hooks 53 face each other. The hook 53 is slid on the hook support portion 5107 so that the screw hole 5301 of the hook 53 faces the elongated hole 5101 of the hook support portion 5107. The screw 55 is fastened into the screw hole 5301 via the elongated hole 5101.

As the flat surface 5305 and the slide projections 5307 of the hook 53 are respectively engaged with the flat surface 5113 and the slide grooves 5115 of the engagement recess 5111 of the connecting member 51, even if the screw 55 is turned with respect to the connecting member 51 to be fastened, the hook 53 does not turn with respect to the connecting member 51. This ensures smooth fastening of the hook 53 by the screw 55.

The function of the fixing instrument 5 according to the first embodiment will be described below.

First, a surgeon dissects the back of a patient to expose the spine as shown in FIG. 1. To fix the posterior spinal fusion members 3 to a plurality of vertebrae 1, the surgeon drives the pedicular screw 34 into the associated vertebra 1 in such a way that the male thread portion 3403 moves toward the associated corpus vertebra 12 through the pediculus arcus vertebra 15 from the surface (dorsal-side surface) of the arcus vertebra 14. In this manner, two pedicular screws 34 are driven into each of a plurality of vertebrae 1 at both sides of the spinous processes 11. At the time the driving of the pedicular screws 34 is completed, the rotational positions of the pedicular screws 34 are adjusted such that the slits 3402 (formed in the cylinder portions 3401 of those pedicular screws 34) are aligned with one another.

Next, the surgeon fits the washers 33 equal in number to the pedicular screws 34 over the associated posterior spinal fusion member 3. The intervals between the individual washers 33 are adjusted in accordance with the intervals between the pedicular screws 34. Then, the surgeon fits the washers 33 in the cylinder portions 3401 of the associated pedicular screws 34 with the posterior spinal fusion member 3 through the slits 3402.

The setscrew 32 is engaged with the female threads on the inner wall of the cylinder portion 3401 of the associated pedicular screw 34 from the top of the cylinder portion 3401.

The surgeon then places the cap 31 over the distal end of the cylinder portion 3401. The surgeon further fastens the setscrew 32 to secure the washer 33 in the cylinder portion 3401, with the hexagonal wrench made to pass through the hole of the cap 31 and engaged with the hexagonal hole of the setscrew 32. The cylinder portion 3401 is widened according to the movement of the setscrew 32, while securing the cap 31. The structure for coupling the pedicular screw 34 driven in the arcus vertebra 14 of the vertebra 1 to the posterior spinal fusion member 3 is not limited to the illustrated type as other various conventional structures may be employed.

Figure 5:
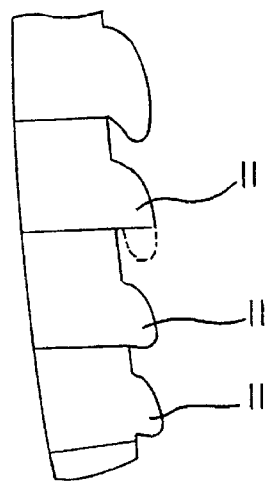
FIG. 5 is a side view as viewed from the arrow V in FIG. 4.

To secure the installing space for the fixing instrument 5, the spinous processes 11 of the vertebra 1 where the fusion instrument 5 is to be anchored are cut off as shown in FIG. 5.

To attach the fixing instrument 5 to the posterior spinal fusion member 3, the surgeon first loosens the screws 55 fitted in both hook support portions 5107 to set the distance between both hooks 53 wider than the distance between both posterior spinal fusion members 3. Under this condition, the surgeon inserts the fixing instrument 5 inside of the body of the patient (not shown) from the dissected portion at the back and makes the engagement surface 5303 of each hook 53 face toward the side of the associated posterior spinal fusion member 3. At this time, the end face of the head 5503 of the screw 55 faces outward through the dissected portion of the patient, and the bottom surface 5505 of the head 5503 comes above the inclined surface 5103 of the inclined recess 5119.

Under this condition, the surgeons inserts the distal end of a hexagonal wrench (not shown) in the body through the dissected portion, and engages it with the hexagonal hole formed in the end face of the head 5503 of the screw 55. Then, the surgeon turns the hexagonal wrench from outside of the body to drive the screw 55 into the hook 53. As the screw 55 is driven, the bottom surface 5505 of the head 5503 of the screw 55 abuts on the inclined surface 5103. In the state that the fixing instrument 5 is attached to the individual posterior spinal fusion members 3, the inclined surface 5103 formed in a recess formed in the top of the hook support portion 5107 of the connecting member 51 is inclined in such a way as to come away more from the associated vertebra 1 in consequence to approach the associated end of the connecting member 51. When the screw 55 is further fastened from the state where the bottom surface 5505 of the screw head 5503 abuts on the inclined surface 5103, the inclination of the inclined surface 5103 causes the head 5503 of the screw 55 to slide toward the shaft portion 5105 in the inclined recess 5119. In accordance with this sliding action, the hook 53 also slides toward the shaft portion 5105. The engagement surface 5303 of the hook 53 engages with the associated posterior spinal fusion member 3 from outside.

When the screw 55 is fastened further from the state where the engagement surface 5303 is in engagement with the associated posterior spinal fusion member 3, the inclined action between the inclined surface 5103 and the bottom surface 5505 of the screw 55 causes the hook 53 to slide further toward the shaft portion 5105. Accordingly, the force is applied to both posterior spinal fusion members 3 to cause those posterior spinal fusion members 3 to approach each other.

If the fixing instruments 5 are anchored to the posterior spinal fusion members 3 at a plurality of positions apart from one another at vertical intervals, the forces from those fixing instruments 5 act on those positions to correct the distortion between the upper and lower vertebrae 1 in the twisting direction.

According to this embodiment, as described above, the fixing instrument 5, which is anchored to a pair of posterior spinal fusion members 3 laid over a plurality of vertically located vertebrae 1 on both sides of the spinous processes 11, includes the connecting member 51, the pair of hooks 53 slidably supported at both ends of the connecting member 51, and the screws 55 which attach the hooks 53 to the connecting member 51. The connecting member 51 includes the shaft portion 5105 and the flat hook support portions 5107 formed at both ends of the shaft portion 5105. Further, the bottom of the recess 5119 formed in the top surface 5117 Of the hook support portion 5107 is formed as the inclined surface 5103, which is inclined in such a way as to come away (i.e., to become shallower) from the associated vertebra 1 in consequence to approach the associated end of the connecting member 51. The screw 55 is inserted through the elongated hole 5101 formed in the inclined surface 5103 to be engaged with the screw hole 5301 of the hook 53.

Fastening the screw 55 therefore causes each hook 53 to slide toward the shaft portion 5105. The sliding of the hooks 53 applies the force to the individual posterior spinal fusion members 3, engaged with the engagement surfaces 5303 of the hooks 53, to make the posterior spinal fusion members 3 approach each other. The force can easily and surely correct the distortion between the vertebrae 1, which cannot be corrected by the posterior spinal fusion members 3 alone, in the twisting direction.

At the time the fixing instrument 5 is attached to the posterior spinal fusion members 3, according to this embodiment, the end face of the head 5503 of the screw 55 faces outward through the dissected portion of the patient. Even if there is limited space around the screw 55 inside the patient's body, a screw fastening tool, such as a hexagonal wrench, can be manipulated without any problem. The Surgeon can thus easily perform an operation to slide the individual hooks 53 in the direction to approach each other. The surgeon can therefore conduct a surgical operation to apply force to the individual posterior spinal fusion members 3 to set them closer to each other.

SECOND EMBODIMENT

A second embodiment of the present invention will now be described with reference to FIGS. 6a to 6c. In those diagrams, the same reference numerals as used in FIGS. 2a through 2c are given to parts corresponding or identical to those of the first embodiment to avoid repeating their descriptions.

A recess 5121 is formed in the top surface 5117 of each hook support portion 5107 at a position closer to the shaft portion 5101 then the recess 5119. The recess 5121 is formed in an oval form of which major axis is laid along the lengthwise direction of the shaft portion 5105.

The bottom of the recess 5121 is formed as an inclined surface 5123. Opposite to the direction of the inclination of the inclined surface 5103 of the recess 5119, the inclined surface 5123 is deeper on the side which is closer to the end of the connecting member 51 and is shallower on the side which is closer to the shaft portion 5105. That is, in the state that the fixing instrument 5A is placed in e patient's body, the inclined surface 5123 is inclined in such a way that the inclined surface 5123 comes closer to the vertebra 1 in consequence to approach the end of the connecting member 51. An elongated hole 5125 is formed In the widthwise center of the inclined surface 5123 elongated along the lengthwise direction of the connecting member 51. This elongated hole 5125 reaches the engagement recess 5111 through the hook support portion 5107.

In addition to two hooks 53A which engage the individual posterior spinal fusion members 3 from outside, similarly to the hooks 53 of the first embodiment, two additional hooks 53B engage with the posterior spinal fusion members 3 from inside are attached to the associated hook Support portions 5107 of the fixing instrument 5A. First, the flat surface 5305 and projections 5307 formed it the proximal end portion of each hook 53B are engaged with the engagement recess 5111 (flat surface 5113 and slide grooves 5115) of the associated hook support portion 5107 similarly to those of the hook 53 of the first embodiment. The directions of both hooks 53B should be adjusted so that the engagement surfaces 5303 of the hooks 53B face away from each other. The hooks 53B are slid on the associated hook support portions 5107 so that the screw hole 5301 of each hook 53B faces the elongated hole 5125 of the hook support portion 5107. Then, the screw 55 is engaged with the screw hole 5301 through the elongated hole 5125. The hooks 53B are slidably attached to the hook support portions 5107 in the manner described above. The screws 55 are fastened to secure the hooks 53B. The flat surface 5305 and the slide projections 5307 formed at the proximal end Of the hook 53B are respectively engaged with the flat surface 5113 and the slide grooves 5115 of the engagement recess 5111 of the connecting member 51 as in the case of the hook 53 of the first embodiment. Even if the screw 55 is turned with respect to the connecting member 51 to be fastened, the hook 53B does not turn with respect to the connecting member 51. This ensures a smooth fastening of the hook 53 by the screw 55.

The hooks 53A are attached to the hook support portions 5107. The flat surface 5305 and the slide projections 5307 formed at the proximal end of the hook 53A are engaged with the engagement recess 5111 of the hook support 5107 the same manner as those of the hook 53 of the first embodiment. The screw 55 is engaged with the screw hole 5301, formed in the proximal end of the hook 53A, through the elongated hole 5101. The hooks 53A are slidably attached to the hook support portions 5107 in the manner described above. The screws 55 are fastened to secure the hooks 53A. The hooks 53A and the hooks 53B, attached to the associated hook support portions 5107, are arranged So that their engagement surfaces 5303 face each other.

The function of the fixing instrument 5 according to the second embodiment will be described below.

As in the first embodiment, the posterior spinal fusion members 3 are fixed to the vertebrae 1 of a patient. Then, the individual screws 55 of the fixing instrument 5A are loosened to set the individual hooks 53A and 53B slidable on the associated hook support portions 5107, and the poster posterior spinal fusion members 3 are positioned between the two paired hooks 53A and 53B. By further fastening the screws 55 engaged with the hooks 53A from the above state, force is applied to the individual posterior spine fusion members 3 to cause those posterior spinal fusion members 3 to approach each other, similarly to the first embodiment.

By fastening the screws 55 engaged with the hooks 53B thereafter, each posterior spinal fusion member 3 is held between the engagement surfaces 5303 of both of the hooks 153A, 53B. Accordingly, the distortion of the upper and lower vertebrae 1 in the twisting direction is corrected.

Therefore, the fixing instrument 5A of the second embodiment can have the same advantages as the fusion instrument 5 of the first embodiment. Additionally, since the hooks 53A and 53B can be securely engaged with the posterior spinal fusion members 3, it is advantageously possible to prevent the fixing instrument 5A from coming off the posterior spinal fusion members 3.

THIRD EMBODIMENT

A third embodiment of the present invention will now be described with reference to FIGS. 7a to 7c.

A fixing instrument 7, according to the third embodiment, includes a connecting member 71 having a length corresponding to the distance between a pair of posterior spinal fusion members 3, and a pair of hooks 73 (corresponding to engagement members) coupled to both ends of the connecting member 71. The connecting member 71 has a rod-like shaft portion 7101 and hook support portions 7103 formed as square rods at both ends of the shaft portion 7101.

The top surfaces of the hook support portions 7103 are level with each other. The bottom of each hook support portion 7103 is formed as an inclined surface 7105 inclined such that the nearer it comes toward the end of the connecting member 71 the more it comes away from the top surface. That is, in the state that the fixing instrument 7 is placed in a patient's body, the inclined surface 7105 is inclined such that the inclined surface 7105 comes closer to the vertebra 1 in consequence to approach the end of the connecting member 71.

A recess 7109 is formed in a top surface 7107 of each hook support portion 7103 in an almond shape elongated along the lengthwise direction of the shaft portion 7101. The bottom of the recess 7109 serves as an inclined surface 7111, which is shallower on the side which is closer to the end of the connecting member 71 and is deeper on the side which is closer to the shaft portion 7101. That is, in the state that the fixing instrument 7 is placed in the patient's body, the inclined surface 7111 is inclined such that the inclined surface 7111 comes away from the vertebra 1 in consequence to approach the end of the connecting member 71. An elongated hole 7113 is formed in the widthwise center of the inclined surface 7111 elongated along the lengthwise direction of the connecting member 71. The elongated hole 7113 penetrates through the bottom 7105 of the hook support portion 7103.

Each hook 73 mentioned above has an arched engagement surface portion 7301 engageable with the associated posterior spinal fusion member 3, and a male thread portion 7303. The engagement surface portion 7301 has the shape of a square rod member bent in an arcuate form. The boundary between the engagement surface portion 7301 and the male thread portion 7303 is formed to have a narrower width, as shown in FIG. 7c. A shoulder 7305 formed by the narrowed width serves as an inclined surface inclined to be parallel to the bottom of the hook support portion 7103 in the state that the hook 73 is attached to the connecting member 71. That is, in the state that the fixing instrument 7 is placed in the patient's body, the inclined surface 7305 is inclined such that the inclined surface 7305 comes closer to the vertebra 1 in consequence to approach the end of the connecting member 71.

To attach each hook 73 to the above-described hook support portion 7103, the male thread portion 7303 of the hook 73 is inserted in the elongated hole 7113. At this time, the directions of both hooks 73 should be adjusted so that the engagement surface portions 7301 of the hooks 73 face each other. A nut 75 (equivalent to a female thread member) is engaged with the male thread portion 7303 on the inclined surface 7111. The bottom of the nut 75 is formed as a tapered, inclined surface 7501. The hooks 73 are slidably attached to the associated hook support portion 7103 in the manner described above. The nuts 75 are fastened to secure the hooks 73.

The function of the fixing instrument 7 according to the third embodiment will be described below.

As in the first embodiment, the posterior spinal fusion members 3 are fixed to the vertebrae 1 of a patient. Then, the individual nuts 75 of the fixing instrument 7 are loosened to slide the individual hooks 73 to set the distance between both hooks 73 wider then the distance between both posterior spinal fusion members 3. Under this condition, the fixing instrument 7 is inserted into the body of the patient through the dissected portion at the back to position each posterior spinal fusion member 3 between the engagement surface portion 7301 of the associated hook 73 and the inclined surface 7105 of the associated hook support portion 7103. The nuts 75 are then fastened.

The fastening of the nuts 75 causes the inclined surfaces 7305 of the hooks 73 to abut on the inclined surfaces 7105 of the associated hook support portions 7103. Alternatively the posterior spinal fusion members 3 abut on the bottom surfaces 7105 of the associated hook support 7103. It is the matter of design choice to make the inclined surface 7305 or the posterior spinal fusion member 3 abut on the inclined surface 7105 of the associated hook support portion 7103 first, or make both abut on the inclined surface 7105 simultaneously.

Further, fastening the nut 75 causes an inclined action between the inclined surface 7501 of the nut 75 and the inclined surface 7111 of the associated hook support portion 7103, and also causes an inclined action between the inclined surface 7105 of the hook Support 7103 and the associated posterior spinal fusion member 3. Those inclined actions slide the hook 73 toward the shaft portion 7101 along the elongated hole 7113. Accordingly, force is applied to the individual posterior spinal fusion members 3 from the associated hooks 73 to cause both posterior spinal fusion members 3 to approach each other.

If the fixing instrument 7 is designed so that the inclined surface 7305 of the hook 73 abuts on the inclined surface 7105 of the associated hook support portion 7103 before the associated posterior spinal fusion member 3, the engagement of the inclined surface 7305 with the inclined surface 7105 causes the hook 73 to slide, thus applying force to the individual posterior spinal fusion members 3 to approach each other.

Therefore, the fixing instrument 7 of the third embodiment can also have the same advantages as the fixing instrument 5 of the first embodiment. Like the second embodiment, the third embodiment has an advantage that the fixing instrument 7 can more surely be prevented from coming off of the posterior spinal fusion members 3.

A part of the male thread portion 7303 of the hook 73 may be shaped to have a rectangular cross section, or flat portions may be formed at to locations 180 degrees apart from each other in the circumferential direction of the male thread portion 7303, whereby the portion having the rectangular cross section or the flat portions engage with both side edges of the elongated hole 7113. In this case, the thickness of the rectangular cross sectional port,ion or the thickness between the flat portions should be made slightly smaller than the width of the elongated hole 7113. This restricts the rotation of the-hook 73 at the time the nut 75 is fastened, thus facilitating the fastening of the hook 73.

According to the third embodiment, the force to shift the individual posterior spinal fusion members 3 toward each other is given by the cam action caused by the sliding contact of the inclined surface 7501 of the nut 75 with the inclined surface 7111 of the hook support portion 7103 or the cam action caused by the sliding contact of the inclined Surface 7305 of the hook 73 with the inclined surface 7111 of the hook support portion 7103. The structure may be modified such that the force to shift the individual posterior spinal fusion members 3 toward each other is applied via the individual hooks 73 to those posterior spinal fusion members 3 by the inclined action caused by the sliding contact of the inclined surface 7105 of each hook support portion 7103 with the cam surface 7305 of the associated hook 73.

Although the engagement surfaces 5303 end the engagement surface portions 7301 of the hooks 53, 53A, 53B and 73 are formed in an arc Shape in the above-described embodiments, the structure of the hook may take various forms in accordance with the shape of the spinal fusion member and is not limited to those depicted in the sections of the individual embodiments.

In short, according to the present invention, the top of the screw head or the end face of the female thread member can be set to face toward the dissected portion of a patient. At the time of sliding the engagement member in the lengthwise direction of the connecting member to apply the force to the spinal fusion members securely fixed to both sides of the spinpus processes of the patient's spine to shift those spinal fusion members toward each other, a screw to drive the engagement member or a tool to fasten a female thread member can easily be manipulated without any problem within a narrow space inside the patient's body.

What is claimed is:

1. A fixing instrument for spinal fusion members for mutually fixing a plurality of spinal fusion members to be secured over a plurality of vertebrae constituting a spine, comprising:

an elongated connecting member, having a on longitudinal axis to be positioned across said plurality of spinal fusion members along said longitudinal axis;

a plurality of engagement members each having engaging portions to engage said spinal fusion members, said engagement members provided on said connecting member and being slidable along said longitudinal axis of said connecting member;

moving members, engaging said engagement members and said connecting member, that are movable in a first direction transverse to said longitudinal axis of said connecting member, by an external operation; and conversion means on said connecting member for converting the movement of said moving members from said first transverse direction to the sliding movement of said engagement members along said longitudinal axis of said connecting member.

2. The fixing instrument for spinal fusion members according to claim 1, wherein said plurality of engagement members includes first and second engagement members, said sliding movement of said first engagement member being in a direction approaching said second engagement member.

3. The fixing instrument for spinal fusion members according to claim 1, wherein said engaging portions comprise hooks, said engaging portions being attached to said moving members, wherein upon said sliding movement of said engagement members along said longitudinal axis of said connecting member, said hooks engage said spinal fusion members.

4. The fixing instrument for spinal fusion members according to claim 3, wherein said plurality of engagement members comprise:

plural pairs of engagement members provided on said connecting member, each pair of said plural pairs of engagement members having a pair of said hooks, wherein a first hook of each of said pair of hooks faces a second pair hook of each of said pair of hooks so that each of said spinal fusion members is clamped between said first and said second hooks of one of said pairs of engagement member.

5. The fixing instrument for spinal fusion members according to claim 1, wherein each of said moving members has a male thread and a head connected to said male thread;

each of said engagement members has a female thread formed to engage with said male thread; and said connecting member has a first and second slot, wherein at least one of said male threads passes through said first slot and at least another of said male threads passes through said second slot.

6. The fixing instrument for spinal fusion members according to claim 5, wherein said conversion means further comprises:

first and second surfaces adjacent each of said first and second slots, wherein said engagement members slide along said first surfaces, and said heads of said moving members slide along said second surfaces; and wherein said conversion means further include a gradually varying thickness between each of said first and second surfaces.

7. The fixing instrument for spinal fusion members according to claim 6, wherein each of said second surfaces is a bottom surface of a recess formed in said connecting member adjacent one of said pair of slots, and wherein each said bottom surface comprises an inclined surface.

8. The fixing instrument for spinal fusion members according to claim 1, wherein each of said moving members comprises a nut having a female thread formed therein;

each of said engagement members comprises a male thread formed to engage with said female thread; and said connecting member comprises a first and second slot, wherein at least one of said male threads passes through said first slot and at least another of said male threads passes through said second slots.

9. The fixing instrument for spinal fusion members according to claim 8, wherein each of said pair of slots passes through an upper surface and a lower surface of said connecting member;

wherein each of said engagement members moves along one of said upper and lower surfaces through which one of said pair of slots passes;

wherein each said nut of each of said moving members moves along the other of said upper and lower surfaces through which one of said pair of slots passes; and wherein a thickness between said upper surface and said lower surface through which each of said pair of slots passes gradually varies.

10. The fixing instrument for spinal fusion members according to claim 9, wherein each of said one of said upper and lower surfaces along which said engagement members move is an inclined surface which is adapted to allow sliding of one of the spinal fusion members therelong, when said engagement members engage with the spinal fusion members.

11. The fixing instrument according to claim 1, wherein each of said moving members is a screw which engages a screw hole provided in each of said engagement members, said fixing instrument further including preventing means comprising a male thread provided on each said screw and a female thread provided on an inner surface of each said screw hole, for preventing said movement of said moving members in said longitudinal direction unless said male threads are moved with respect to said female threads.

12. The fixing instrument for spinal fusion members according to claim 1, further comprising:

means for preventing a movement of said moving members in direction opposite to said longitudinal direction.

13. A fixing instrument for spinal fusion members for mutually fixing a plurality of spinal fusion members to be secured over a plurality of vertebrae constituting a spine, comprising:

a connecting member to be positioned across said plurality of spinal fusion members, said connecting member comprising an elongated hole formed near a first end of said connecting member and extending in a longitudinal direction of said connecting member;

an engagement member attached to said first end of said connecting member, said engagement member having an engaging portion to engage one of said spinal fusion members, said engagement member being slidable along said longitudinal direction of said connecting member;

a moving member which connects with said engagement member through said elongated hole, said moving member being movable in a direction transverse to said longitudinal direction of said connecting member; and conversion means on said connecting member for converting the movement of said moving member in said direction transverse to said longitudinal direction to the movement of said engagement member in a direction substantially aligned with said longitudinal direction of said connecting member.

14. A fixing instrument to be anchored to a pair of elongated spinal fusion members attached on both sides of spinous processes of a plurality of vertebrae positioned vertically and arranged along a direction of said vertebrae, comprising:

a connecting member formed to have a length corresponding to a distance between said pair of spinal fusion members, said connecting member having first and second ends;

a pair of first engagement members, one of said pair of first engagement members being coupled to said first end of said connecting member, and the other of said pair of first engagement members being coupled to said second end of said connecting member, said pair of first engagement members adapted to be engaged with said spinal fusion members; and coupling means for coupling said engagement members to said connecting member, said coupling means comprising:

recesses formed in said first and second ends of said connecting member, said recesses each having a predetermined length in a longitudinal direction of said connecting member and each comprising an inclined bottom surface, wherein each said inclined surface makes each said recess deeper within said connecting member, at an end of said predetermined length nearer a center of said connecting member, than at an end of said predetermined length nearer one of said first and second ends of said connecting member;

an elongated hole formed in each of said inclined bottom surfaces and extending in said longitudinal direction;

a screw hole formed in a top surface of each of said first engagement members;

a screw insertable through each of said elongated holes, each said screw comprising a head corresponding to a diameter of each of said respective recesses, capable of contacting each said bottom surface of each said recess, wherein said screws are inserted into said elongated holes to engage with said screw holes.

15. The fixing instrument for spinal fusion members according to claim 13, further comprising:

a pair of second engagement members, wherein one of said pair of second engagement members is coupled to a portion of said connecting member adjacent one of said pair of first engagement members, and the other of said pair of second engagement members is coupled to a portion of said connecting member adjacent the other of said pair of first engagement members, for holding spinal fusion members in cooperation with said pair of first engagement members, wherein each of the spinal fusion members is held by one of said pair of first engagement members and one of said pair of second engagement members; and second coupling means for coupling said pair of second engagement members to said connecting member, said second coupling means comprising:

second recesses formed near said first and second ends of said connecting member, said second recesses each having a second predetermined length in a longitudinal direction of said connecting member and comprising a second inclined bottom surface, wherein each said second inclined surface makes each said second recess deeper within said connecting member, at an end of said predetermined length nearer one of said first and second ends of said connecting member than at an end of said predetermined length nearer a center of said connecting member;

a second elongated hole formed in each of said second inclined bottom surfaces and extending in said longitudinal direction;

a second screw hole formed in a top surface of each of said second engagement members;

a screw insertable through each of said second elongated holes, each said screw comprising a head corresponding to a diameter of each of said respective second recesses, capable of contacting each said second bottom surface of each said second recess, wherein said second screws are inserted into said second elongated holes to engage with said second screw holes;

wherein advancing said screws into said screw holes and said second screws into said second screw holes biases said first and second engagement members toward one another, along said longitudinal direction, to engage and hold the spinal fusion members.

* * * * *

UNITED STATES PATENT AND TRADEMARK OFFICE
CERTIFICATE OF CORRECTION

PATENT NO. : 5,569,246
DATED : October 29, 1996
INVENTOR(S) : S. OJIMA et al.

It is certified that error appears in the above-indentified patent and that said Letters Patent is hereby corrected as shown below:

At column 10, line 37 (claim 1, line 5), delete "on".

At column 11, line 8 (claim 4, line 8), delete "pair" (first occurrence).

At column 11, line 11 (claim 4, line 11), change "member" to ---members---.

At column 12, line 11 (claim 12, line 4), after "in" insert ---a---.

Signed and Sealed this

Thirteenth Day of May, 1997

BRUCE LEHMAN

*Attest:*

*Attesting Officer*     Commissioner of Patents and Trademarks